United States Patent
Gross

(10) Patent No.: US 9,452,269 B2
(45) Date of Patent: Sep. 27, 2016

(54) METHOD, RETENTION DEVICE AND MEDICAL TREATMENT DEVICE FOR STABLE SUPPORT OF A NEEDLE TO BE INSERTED INTO A PATIENT

(75) Inventor: Patrick Gross, Langensendelbach (DE)

(73) Assignee: Siemens Aktiengesellschaft, Munich (DE)

( * ) Notice: Subject to any disclaimer, the term of this patent is extended or adjusted under 35 U.S.C. 154(b) by 454 days.

(21) Appl. No.: 13/173,249

(22) Filed: Jun. 30, 2011

(65) Prior Publication Data

US 2012/0004681 A1    Jan. 5, 2012

(30) Foreign Application Priority Data

Jul. 2, 2010   (DE) .................. 10 2010 025 921

(51) Int. Cl.
  *A61B 17/34*   (2006.01)
  *A61M 5/46*    (2006.01)
  *A61M 5/00*    (2006.01)
  *A61M 5/42*    (2006.01)

(52) U.S. Cl.
  CPC ............. *A61M 5/46* (2013.01); *A61M 5/001* (2013.01); *A61M 5/427* (2013.01)

(58) Field of Classification Search
  CPC ............... A61B 17/3403; A61B 2017/3407; A61M 39/04; A61M 5/001; A61M 5/46
  USPC .................... 606/185; 604/117, 52
  See application file for complete search history.

(56) References Cited

U.S. PATENT DOCUMENTS

| | | | |
|---|---|---|---|
| 2,238,323 A | | 11/1939 | Hollingsworth |
| 3,955,558 A | * | 5/1976 | Fuisz ............................ 600/573 |
| 4,232,784 A | * | 11/1980 | Hesselgren ................... 206/210 |
| 4,332,248 A | * | 6/1982 | DeVitis ......................... 604/179 |
| 4,392,859 A | | 7/1983 | Dent |
| 4,755,170 A | * | 7/1988 | Golden .......................... 604/513 |
| 4,784,646 A | * | 11/1988 | Feingold ....................... 604/175 |
| 4,857,053 A | * | 8/1989 | Dalton ..................... 604/288.02 |
| 5,120,321 A | * | 6/1992 | Oksman et al. .............. 604/198 |
| 5,123,907 A | * | 6/1992 | Romaine ....................... 606/131 |
| 5,292,325 A | * | 3/1994 | Gurmarnik ................... 606/108 |
| 5,372,252 A | * | 12/1994 | Alexander .................... 206/210 |
| 5,437,640 A | * | 8/1995 | Schwab ........................ 604/116 |
| 5,554,127 A | * | 9/1996 | Crouther et al. ............. 604/192 |
| 6,036,632 A | * | 3/2000 | Whitmore et al. ............... 600/7 |
| 6,482,187 B1 | * | 11/2002 | Gibbs ........................... 604/218 |
| 6,579,262 B1 | * | 6/2003 | Mick et al. ................... 604/116 |
| 8,231,734 B2 | * | 7/2012 | Johnsen et al. .................... 134/6 |
| 2004/0073106 A1 | * | 4/2004 | Lee et al. ...................... 600/415 |
| 2004/0243146 A1 | | 12/2004 | Chesbrough et al. |
| 2007/0233157 A1 | * | 10/2007 | Mark et al. ................... 606/130 |
| 2009/0118662 A1 | | 5/2009 | Schnall |

(Continued)

FOREIGN PATENT DOCUMENTS

| | | |
|---|---|---|
| CN | 201394056 Y | 2/2010 |
| DE | 296 05 069 U1 | 8/1996 |
| EP | 0 182 682 A1 | 5/1986 |

*Primary Examiner* — Eric Rosen
*Assistant Examiner* — Julie Szpira
(74) *Attorney, Agent, or Firm* — Schiff Hardin LLP

(57) ABSTRACT

A method for stable support of a needle to be introduced into a patient, a body to be penetrated by the needle is arranged on the patient. The body is made of a substance corresponding in terms of its mechanical properties to body tissue (in particular corresponding to body tissue in terms of visco-elastic coefficients and density) and/or is made of a gel-like substance.

16 Claims, 1 Drawing Sheet

(56) References Cited

U.S. PATENT DOCUMENTS

| | | |
|---|---|---|
| 2009/0149812 A1 | 6/2009 | MacAulay |
| 2009/0292244 A1* | 11/2009 | Flagle et al. .................. 604/116 |
| 2011/0015659 A1* | 1/2011 | Matsumoto .................. 606/167 |
| 2011/0257594 A1* | 10/2011 | Lacoursiere et al. ......... 604/117 |

\* cited by examiner

METHOD, RETENTION DEVICE AND MEDICAL TREATMENT DEVICE FOR STABLE SUPPORT OF A NEEDLE TO BE INSERTED INTO A PATIENT

BACKGROUND OF THE INVENTION

1. Field of the Invention

The present invention concerns a method for stable support of a needle (in particular an elongated needle) to be inserted into a patient, as well as a retention device for such a needle and a medical treatment device embodying the retention device and a needle.

2. Description of the Prior Art

In the medical field, minimally-invasive procedures are frequently conducted with medical instruments, in particular with needles. In addition to biopsy needles, other examination and treatment needles are known, for example for ablative tumor treatments and the like. The path to the treatment location (site) is frequently planned and or monitored using image exposures. It is known to initially insert the needle only partially in order to then produce an additional image exposure. The danger exists that the needle will fall out of the patient again or rotate in the patient, which is due to the weight of the needle that is still located extra-corporeally. The use of extremely stable retention devices is disadvantageous since the patient or the organs may move.

A simple solution is to support the needle by hand or with a tool held in the hand. This is disadvantageous, however because the hand or the tool could prevent the image acquisition, for example by being located in the image acquisition path or in the image acquisition volume. The image quality can consequently decrease, or the hand directing the tool or the instrument can be exposed to irradiation. Moreover, the manual retention of the needle is not ergonomic and occupies one hand of the person holding the needle.

Another approach is the use of rigid or semi-rigid retention devices, for example robot arms. However, such retention devices must be specifically positioned and then arrested. They do not represent a good compromise between retention and flexibility. Furthermore, they constitute additional equipment in the sterile area, which raises additional problems and requires additional steps to maintain sterility. Moreover, the costs of such systems are typically very high.

SUMMARY OF THE INVENTION

An object of the present invention is to provide a stable manner of supporting such a needle that satisfies the requirements with regard to patient movement while also enabling a reliable retention.

This object is achieved by a method of the aforementioned type wherein, in accordance with the present invention, a body to be penetrated by the needle is arranged on the patient, this body being made from a substance corresponding in terms of its mechanical properties to body tissue (in particular corresponding to body tissue in terms of visco-elastic coefficients and density) and/or a gel-like substance.

Thus a gel-like body and/or a tissue-like body (for example a gel block) is placed on the patient adjacent to the proposed puncture point, and this body holds (supports) a portion of the needle in a flexible manner after the partial penetration of the needle or the instrument into the patient. Retention of the needle is achieved in a way that not only is simple to realize and cost-effective, but also satisfies the special requirements with regard to the patient movement (for example breathing movements or heart movements), even with regard to the sterile environment. For example, the body can be a disposable product for only a single procedure, or it can be designed so as to be sterilized easily.

Before beginning the procedure, the tissue-like and/or gel-like body is placed adjacent to the puncture point on the skin of the patient. In order to conduct the procedure, the needle then pierces through the body and partially into the patient. The needle is then sufficiently supported by the body, such that an image exposure can be taken without additional retention devices being necessary. If it is necessary for the needle to penetrate deeper into the patient in the further course of the procedure, depending on its physical composition the gel body can be slid out of the way or can even be manually cut off and removed by the operator.

As mentioned, the present invention is concerned with examination and/or treatment needles that represent the instrument (thus the tool) itself within the scope of a minimally-invasive procedure, in particular in contrast to needles that are used for injections as part of an injection procedure or injection device. Different entrance paths that are precisely planned using image exposures (which entrance paths can then be checked via an additional image acquisition) are only present in the case (use) of examination and/or treatment needles of this type. In other words, the method in particular concerns the stable bearing of needles of the type for which an entrance path was planned using at least one image exposure and/or is checked using an image exposure after the at least partial insertion of the needle.

In terms of shape, the body used according to the invention can be, for example, cuboid, and it can naturally be flexibly adapted to the surface of the patient as soon as it is placed on this surface. Furthermore, it is particularly advantageous for the body to be at least partially transparent, meaning that the skin of the patient is still recognizable to the handler through the body, for example if markers are provided on the skin or an optical (for example laser-assisted) navigation assistance system is provided.

Furthermore, the body can be formed of a substance that is visible in the image acquisition technique that is used, for example is visible in magnetic resonance imaging or CT imaging. This can enable the course of the instrument to be tracked over a longer range, even outside of the body (for example by means of an automatic image evaluation), such that a better estimation of the current alignment of the needle is enabled.

A body made of a biocompatible substance and/or a gel (in particular of agar-agar and/or gelatin) can appropriately be used. The use of a biocompatible substance is recommended when it may occur (due to the specific properties of the substance) that a portion of the substance may be carried into the body of the patient upon being pierced by the needle. In embodiments in which it is ensured that this cannot occur (for example if the body has prefabricated passage openings through which the needle can be directed), a material that is not biocompatible can be used.

The substance can be selected so that it has a disinfecting and/or blood-coagulating effect. In this way the substance (in the case of a disinfecting effect) supports the maintenance of the sterile region during the procedure, whereas blood clotting is supported given a coagulating effect.

A body that adheres to the side facing toward the patient is appropriately used. This avoids sliding of the body after it has been initially attached to the body. The adhesive effect is preferably be achieved by the substance itself, but it is also possible to provide a layer having an adhesive property on one side of the body.

In a further embodiment, the body can additionally be used as an orientation aid. For this purpose, the tissue-like and/or gel-like body can, for example, have markings on the top or bottom, for example a grid or the like, and can simultaneously be fashioned to be transparent so that, when the needle penetrates the body, the handler receives an orientation aid as to how the needle is presently oriented. An advantageous embodiment results when the body—which, in general, ultimately represents an artificial (at least as far as the mechanical properties are concerned) tissue extension—is visible in the employed image acquisition technique. The user can then achieve an improved orientation or navigation of the needle using the markings that are very well visible in the image acquisition and are seen by the user on the gel body.

The selection of the substance forming the body should be made so that its rigidity is sufficient to prevent the substance from independently flowing in the typical time scales for such procedures and to prevent the body from making any other noteworthy independent shape changes.

In addition to the method, the present invention concerns a retention device for a needle to be introduced into a patient, that includes a body to be pierced by the needle and to be placed on the patient, the body being made of a substance corresponding to body tissue in terms of mechanical properties (in particular corresponding to body tissue in visco-elastic coefficients and density) and/or corresponding to a gel-like substance.

All statements above concerning the body and the method apply analogously to the retention device according to the invention. The above statements concerning the body itself apply to the retention device as well. All embodiments of, and advantages achieved with, the body as described above apply to the retention device as well.

The body can be essentially cuboid and/or transparent. Furthermore, the body may be formed of a biocompatible substance and/or a gel, in particular agar-agar and/or gelatin. A biocompatible substance should always be used when the risk exists that a part of the body may be carried into the patient upon being punctured with the needle. In order to additionally support the processes during a procedure, the substance can have a disinfecting and/or blood-coagulating effect, for example due to an appropriate additive.

The body can be fashioned to be adhesive on a side thereof facing toward the patient. This can originate from properties of the substance itself; or an adhesive layer can be provided on one side of the body, for example.

In an embodiment of the retention device, on the side facing toward the patient the body can be provided with a geometric marking, in particular with a regular recessed pattern. In addition to a recessed pattern (that, for example, can depict a grid pattern serving for orientation) it is naturally also possible to provide markings (for example as dye layers or the like) on the side facing toward the patient. It is then particularly advantageous for the body to be essentially transparent, meaning that the user viewing the body from above can recognize the markings facing toward the patient and orient on these. In a version of this embodiment, the body can also have a geometric marking (in particular a regular recessed pattern) on the side facing away from the patient. For example, the user can thus track whether the entrance point and the exit point of the needle from the body of the retention device are offset, and the like. These markings can be particularly advantageously combined with an embodiment of the substance such that it is visible in the image acquisition technique that is used, thus for example it is MR-visible and/or CT-visible. The body can then also be detected in image exposures that are made for planning and/or monitoring of the procedure, and for example in one embodiment of the marking as grooves these can also be visible in the image exposures, such that overall an excellent orientation aid for the physician results.

The present invention also concerns a medical treatment device that includes a needle to be introduced into a patient and a retention device according to the invention. With such a treatment device, a procedure can be implemented with an improved retention of the needle.

DESCRIPTION OF THE PREFERRED EMBODIMENTS

Figure 1:
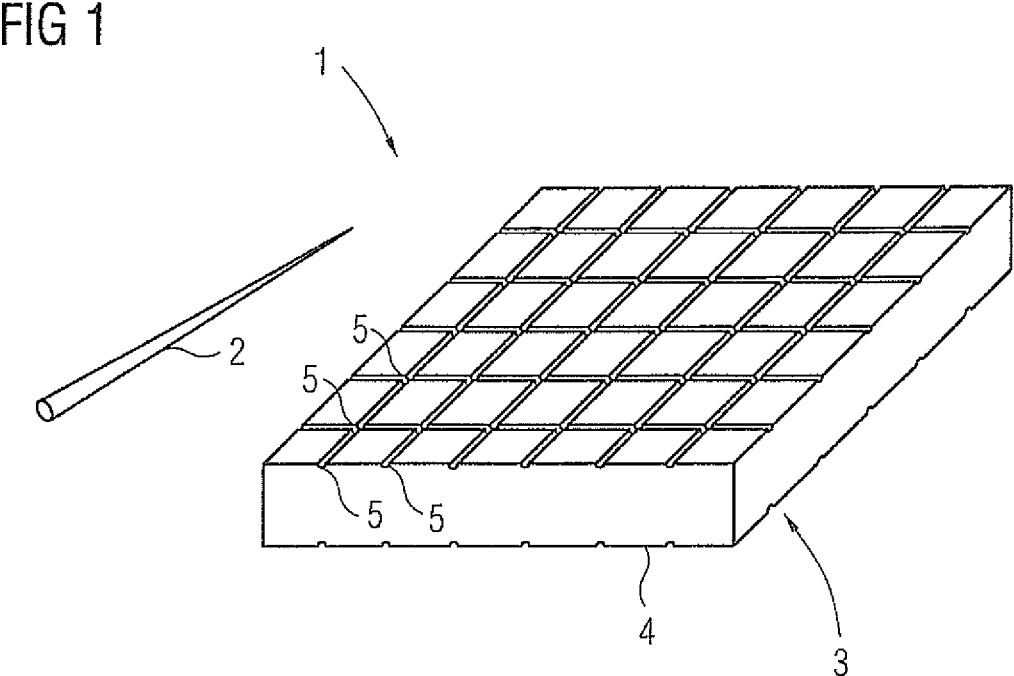
FIG. 1 shows a treatment device according to the invention.

FIG. 1 shows a medical treatment device 1 according to the invention; in addition to a needle 2 that, for example, can be fashioned as a typical biopsy needle, said medical treatment device 1 has a retention device 3 with a body 4 made of a gel-like substance corresponding to a body tissue in terms of the visco-elastic coefficient and density. The substance is furthermore biocompatible and, in the present exemplary embodiment, visible in CT exposures that should be used for procedure planning and monitoring of the procedure.

The basic transparent body 4 is essentially cuboid and respectively has a geometric marking on its top side and on its underside, which geometric markings are presently manifested in the form of regular grooves 5 which as a whole form a regular grid pattern. Since the body 4 is transparent, both the grooves 5 on the top side and the grooves 5 on the underside are apparent to a handler. At this point it is further noted that FIG. 1 shows a schematic drawing and the grooves can in reality also be designed differently, in particular narrower or wider.

The substance of the body 4 is also selected so that it adheres to the skin of a patient when it is placed there, at least insofar as that it cannot slide unintentionally.

The substance of the body 4 can also have a disinfecting effect and a blood-coagulating effect, for example in that corresponding additives are added.

Figure 2:
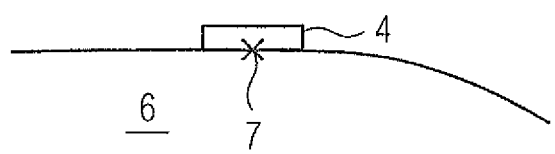
FIGS. 2 and 3 are illustrations to explain the method according to the invention.
Figure 3:
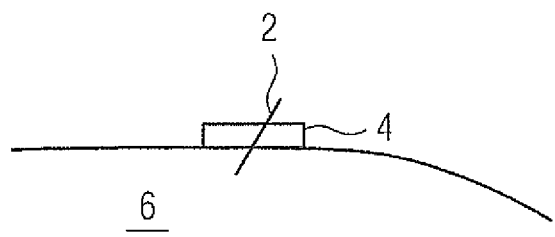

FIG. 2 and FIG. 3 now explain the use of the treatment device 1 according to the invention or, respectively, the retention device 3 according to the invention. For this purpose, in both FIG. 2 and FIG. 3 the surface of a patient 6 is indicated into which the needle 2 should be inserted through a penetration point 7 or into a penetration area for examination or treatment. For this the body 4, which has mechanical properties similar to that of tissue, is initially placed on the patient 6 and thereby adapts to the surface of the patient due to its flexible properties. It does not slide due to the adhesive effect. Therefore (see FIG. 3) the needle 2 can now penetrate to a certain extent through the body 4 into the patient 6, and nevertheless thereby is stable against failing out or rotating due to the body 4. The grooves 5 assist the handler in the insertion of the needle. Since the body 4 is also visible in the image acquisition that now follows, the orientation is additionally improved since the grooves 5 are also detectable in the image and the user can also continue to use these for orientation.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for providing stable support of a needle to be introduced into a patient, comprising the steps of:
   on an extracorporeal surface of a patient, placing a bottom surface of body at a location over a site to be penetrated by a needle, said body also having a top surface consisting of uninterrupted support material completely throughout said body so that said body has no pre-formed open passages between said top surface and said bottom surface, said support material exhibiting material strength properties that self-support said needle selected from the group consisting of a visco-elastic coefficient and density; and
   independently of said body, selecting a non-perpendicular angle with respect to said extracorporeal surface of the patient and inserting said needle into said site at the selected non-perpendicular angle, by first piercing said top surface of said body with said needle and passing said needle in a path through said top and bottom surfaces and through a volume in said body consisting entirely of said support material into said site and mechanically self-supportingly holding said needle along an entirety of said path solely with said volume of said support material to maintain said needle at said selected non-perpendicular angle at said site.

2. The method as claimed in claim 1 comprising employing support material selected from the group consisting of biocompatible materials, agar-agar, and gelatin.

3. The method as claimed in claim 1 comprising employing support material having a disinfecting effect.

4. The method as claimed in claim 1 comprising employing support material having a blood-coagulating effect.

5. The method as claimed in claim 1 comprising employing a transparent support material.

6. The method as claimed in claim 1 comprising employing-support material having an adhesive effect on a side of said body facing said extracorporeal surface of the patient.

7. The method as claimed in claim 1 comprising configuring said body with visually perceptible needle orientation aids.

8. A retention device for providing stable support of a needle to be introduced into a patient, comprising:
   a body having a bottom surface configured for placement on an extracorporeal surface of a patient, at a location over a site to be penetrated by a needle, said body also having a top surface and consisting of uninterrupted support material completely throughout said body so that said body has no pre-formed open passages between said top surface and said bottom surface, said support material exhibiting material strength properties that self-support said needle selected from the group consisting of a visco-elastic coefficient and density; and
   said body being penetrable, at a selected non-perpendicular angle that is selectable with respect to said extracorporeal surface independently of said body by said needle to allow insertion of the needle into said site by first piercing said top surface of said body with said needle and passing said needle in a path through said top and bottom surfaces and through a volume in said body consisting entirely of said support material into said site, said support material of said body having a mechanical strength to self-supportingly hold said needle along an entirety of said path solely with said volume of said support material to maintain said needle at said selected non-perpendicular angle at said site.

9. The retention device as claimed in claim 8 wherein said support material is selected from the group consisting of biocompatible materials, agar-agar, and gelatin.

10. The retention device as claimed in claim 8 wherein said support material has a disinfecting effect.

11. The retention device as claimed in claim 8 wherein said support material has a blood-coagulating effect.

12. The retention device as claimed in claim 8 wherein said support material is transparent.

13. The retention device as claimed in claim 8 wherein said support material has an adhesive effect on a side of said support material facing said extracorporeal surface of the patient.

14. The retention device as claimed in claim 8 wherein said body comprises visually perceptible needle orientation aids.

15. A medical treatment device comprising:
   a needle adapted for insertion into a patient at an insertion site;
   a retention device comprising a body having a bottom surface configured for placement on an extracorporeal surface of a patient, at a location over a site to be penetrated by a needle, said body also having a top surface and consisting of uninterrupted support material completely throughout said body so that said body has no pre-formed open passages between said top surface and said bottom surface, said support material exhibiting material strength properties that self-support said needle selected from the group consisting of a visco-elastic coefficient and density; and
   said body being penetrable, at a selected non-perpendicular angle that is selectable with respect to said extracorporeal surface independently of said body by said needle to allow insertion of the needle into said site by first piercing said top surface of said body with said needle and passing said needle in a path through said top and bottom surfaces and through a volume in said body consisting entirely of said support material into said site, said support material of said body having a mechanical strength to self-supportingly hold said needle along an entirety of said path solely with said volume of said support material to maintain said needle at said selected non-perpendicular angle at said site.

16. The medical treatment device as claimed in claim 15, wherein said needle has a smooth exterior allowing complete withdrawal of said needle from said site through said body with said body remaining intact on said extracorporeal surface of the patient.

* * * * *